US010408714B2

(12) United States Patent
Vethe et al.

(10) Patent No.: US 10,408,714 B2
(45) Date of Patent: Sep. 10, 2019

(54) APPARATUS FOR A FLUID TRANSPORT PIPELINE, RELATED METHOD AND SYSTEM

(75) Inventors: Eivind Vethe, Bergen (NO); Bruno Pinguet, Lormes (FR); Bernard E Theron, Aberdeen (GB); Erik Sjurseth, Bergen (NO)

(73) Assignees: Framo Engineering AS, Bergen (NO); Schlumberger Technology Corporation TX (US)

( * ) Notice: Subject to any disclaimer, the term of this patent is extended or adjusted under 35 U.S.C. 154(b) by 670 days.

(21) Appl. No.: 13/981,307

(22) PCT Filed: Jan. 24, 2012

(86) PCT No.: PCT/EP2012/051066
§ 371 (c)(1),
(2), (4) Date: Oct. 31, 2013

(87) PCT Pub. No.: WO2012/101133
PCT Pub. Date: Aug. 2, 2012

(65) Prior Publication Data
US 2014/0041463 A1    Feb. 13, 2014

(30) Foreign Application Priority Data
Jan. 24, 2011   (GB) .................... 1101186.3

(51) Int. Cl.
*G01N 1/20*      (2006.01)
*E21B 41/04*    (2006.01)
(Continued)

(52) U.S. Cl.
CPC ........... *G01N 1/2035* (2013.01); *E21B 41/04* (2013.01); *E21B 49/08* (2013.01); *F16L 41/021* (2013.01);
(Continued)

(58) Field of Classification Search
CPC ... E21B 41/04; E21B 49/08; G01N 2001/205; G01N 2001/2064; G01N 1/2035; F16L 41/021
(Continued)

(56) References Cited

U.S. PATENT DOCUMENTS 3,242,739 A * 3/1966 Botkin ................. G01N 1/2035
73/863.57
3,400,575 A * 9/1968 Madden .............. G01N 1/2035
210/321.84
(Continued)

FOREIGN PATENT DOCUMENTS

GB          2364134         1/2002
WO       2008/056097       5/2008
(Continued)

OTHER PUBLICATIONS

E. Kelner, "Development and Testing of an ROV-Deployed Deepwater Subsea Sampling System," The Americas Workshop, 26, Apr. 2011 pp. 1-10, XP55042885.

*Primary Examiner* — Helen C Kwok
*Assistant Examiner* — Nashmiya S Fayyaz
(74) *Attorney, Agent, or Firm* — Conley Rose, P.C.

(57) ABSTRACT

Apparatus for use in sampling multiphase fluid in a fluid transport pipeline, the apparatus comprising: a process fluid conduit comprising a blind leg connected to an upstream section and a downstream section; and wherein a fluid sampling port is provided in the blind leg.

28 Claims, 8 Drawing Sheets

(51) Int. Cl.
  *E21B 49/08* (2006.01)
  *F16L 41/02* (2006.01)
  *F16L 41/00* (2006.01)

(52) U.S. Cl.
  CPC .............. *G01N 2001/205* (2013.01); *G01N 2001/2064* (2013.01)

(58) Field of Classification Search
  USPC .............. 73/863.81, 863.51, 863.41, 863.58
  See application file for complete search history.

(56) References Cited

U.S. PATENT DOCUMENTS

| | | | | |
|---|---|---|---|---|
| 4,905,505 | A * | 3/1990 | Reed | G01N 7/00 73/64.46 |
| 5,337,603 | A * | 8/1994 | McFarland | G01F 1/206 73/202 |
| 6,128,962 | A | 10/2000 | Marrelli et al. | |
| 6,435,279 | B1 | 8/2002 | Howe et al. | |
| 6,453,926 | B1 * | 9/2002 | Baker | B01F 5/0473 137/3 |
| 6,532,826 | B1 | 3/2003 | Dou | |
| 2003/0110870 | A1 * | 6/2003 | Bigalke | G01N 1/2035 73/863.85 |
| 2010/0059221 | A1 | 3/2010 | Vannuffelen et al. | |
| 2018/0010944 | A1 * | 1/2018 | Xie | G01F 1/74 |

FOREIGN PATENT DOCUMENTS

| | | |
|---|---|---|
| WO | 2010/106499 | 9/2010 |
| WO | 2010/106500 | 9/2010 |
| WO | 2011/096823 | 8/2011 |

* cited by examiner

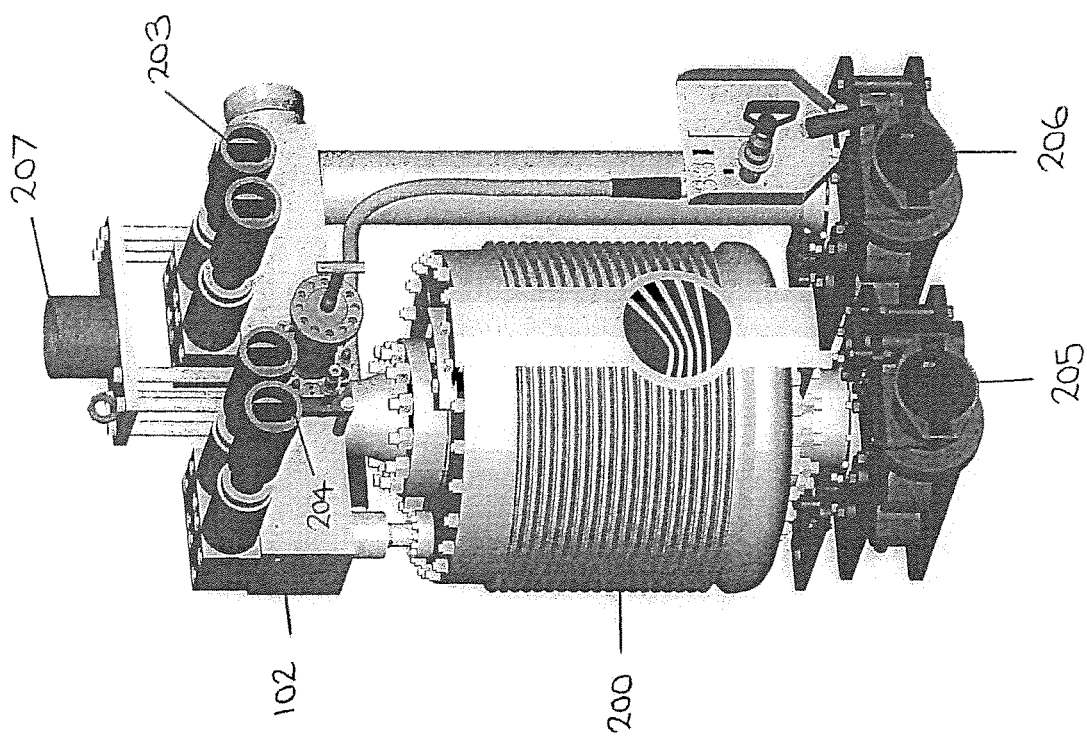

APPARATUS FOR A FLUID TRANSPORT PIPELINE, RELATED METHOD AND SYSTEM

FIELD OF THE INVENTION

The invention relates to apparatus for a fluid transport pipeline, related method and system, particularly for use when transporting multiphase fluids (such as mixtures of oil, water and gas) in the field of hydrocarbon (oil and gas) exploration and production. It has particular application in enabling the sampling of multiphase fluids in a location above ground (commonly known as "topside") or under water (commonly known as "sub-sea"). It can particularly be used to enable the sampling of fluids to allow measurements to be made of liquid and gas in multi-phase and/or "Wet Gas" (see definition below) fluid applications.

BACKGROUND OF THE INVENTION

Multi-phase fluids typically comprise both gas and liquid components and an example would be a well stream extracted from a topside or sub-sea well which comprises a mixture of gas, oil, water and some salt components. Such a mixture can vary substantially as regards the proportions of its gas and liquid components. In the context of this invention the term "fluid" includes a liquid-phase alone (including multiple liquid phase fluids, e.g. a mixture of oil and water), a gas-phase alone, or a combination of gas and liquid phases.

Multi-phase mixtures with a very high gas volume fraction (GVF) are known as condensate or "Wet Gas"—a geological term for a gaseous mixture of hydrocarbons that contain a significant amount of compounds with molecular weights heavier than methane. Such wet gas fluids typically have a GVF of above approximately 95% corresponding to a gas liquid ratio (GLR) above 20. Typically such fluids also contain other non-hydrocarbon compounds such as carbon dioxide, hydrogen sulphide, nitrogen, oxygen and water.

One arrangement for sampling fluids from a hydrocarbon well-bore is known from U.S. Pat. No. 6,435,279 in which a multi-phase fluid is collected from a well-bore using a self-propelled underwater vehicle. The vehicle comprises a collection device and a storage device, and is arranged to collect a sample of the multi-phase fluid from the well-bore and store the collected fluid in the storage device. The vehicle is then moved to a location where the collected sample of fluid can be recovered to enable measurements to be performed on the collected sample.

A drawback with this known arrangement is that the pressure and/or temperature are not maintained between taking a sample from the sample point on the well bore and testing the sample at the remote location, i.e. isobaric and isothermic conditions are not necessarily maintained. This may compromise the sample quality, i.e. representativeness of each phase, and limit the usefulness of the sample. Thus, the gas/liquid ratio at the sample measurement location may not be representative of the gas/liquid ratio at the sample extraction location. Furthermore, phase transitions may occur and/or mass transfer between the phases, resulting in samples that are not compositionally representative. It is preferable that the sampling process does not alter the phase composition.

Samples for the purpose of updating pressure-volume-temperature data for a multiphase flow-meter have to be taken in close proximity to a multiphase flow-meter, otherwise fluid and gas composition of a sampled fluid might be different due to different pressure and temperature elsewhere in a pipeline, and possible release of some of the gas present inside the oil at higher pressure.

There may be several reasons for obtaining a multiphase or wet gas sample, such as: (i) to reduce multiphase metering uncertainty; (ii) for reservoir and production management; (iii) to obtain well chemistry and flow assurance information per well; and (iv) to obtain information for subsea processing.

The invention seeks to provide for a conduit, related method and system offering advantages over known such conduits, methods and systems, and provides an improved conduit, method and system for sampling multiphase fluids.

SUMMARY OF THE INVENTION

According to one aspect of the present invention, there is provided apparatus for use in sampling multiphase fluid in a fluid transport pipeline, the apparatus comprising: a process fluid conduit comprising a blind leg connected to an upstream section and a downstream section; and wherein a fluid sampling port is provided in the blind leg.

Optionally, a second sampling port is provided in the conduit, either upstream or downstream of the blind leg and the apparatus may further comprise means for recirculating fluid from the first sampling port in the blind leg to the second sampling port. In such an arrangement, the recirculating means may comprise an arrangement of sampling conduits and valves provided between said first sampling port and said second sampling port, and at least one sample recovery port may be provided.

The arrangement of sampling conduits optionally may be configured to allow fluid extracted from said first sampling port to be conveyed to at least one of said second sampling port or said sample recovery port.

Optionally, the recirculating means may comprise a sampling tool or a remotely operated vehicle.

When the conduit is in an optional first configuration, the downstream section may extend substantially vertically upwards from said conduit and said second sampling port may be located in an uppermost part of the wall of the conduit in said upstream section.

When the conduit is in an optional second configuration, the downstream section may extend substantially vertically downwards from said conduit and said second sampling port may be located in an uppermost part of the wall of the conduit in the said upstream section.

Optionally, the first sampling port may be located in a wall of the blind leg of the conduit.

The arrangement of sampling conduits optionally may include double-block valves and/or may be heated and/or may be at least partially surrounded by heat conductive material and/or a layer of insulating material.

According to another aspect of the present invention, there is provided a method of sampling fluid from a multi-phase hydrocarbon stream in a conduit, comprising: connecting a first sampling port in a blind leg of the conduit to a second sampling port upstream of the blind leg and maintaining substantially isobaric and isothermic conditions in the fluid flowing from the first sampling port to the second sampling port before taking at least one measurement of a sample.

Optionally, the method may further comprise connecting the first sampling port to the second sampling port via a sampling tool.

The method may also comprise steps of performing at least one measurement on said sample in said sampling tool.

Optionally, the sampling tool may be controlled remotely, e.g. by a remotely operated system, tool or vehicle.

The sampling tool may be permanently installed. Alternatively it may be temporarily deplayed and attachable and detachable via connections such as quick fit or hot-stab connections.

According to another aspect of the present invention, there is provided a system for sampling fluid from a multiphase hydrocarbon stream comprising a conduit comprising any one or more of the features described above, and a remotely operated vehicle comprising means to connect the first sampling port to the second sampling port and to recirculate fluid from the first port to the second port for a predetermined time at substantially isothermal and isobaric conditions.

Optionally, the remotely operated vehicle may comprise means to perform measurements on the recirculating fluid at isothermic and isobaric conditions.

Further optionally, the vehicle may comprise means to extract a sample of the fluid in at least one sealable container.

According to yet a further aspect of the present invention, there is provided apparatus for use in sampling multiphase fluid in a fluid transport pipeline, the apparatus comprising: a process fluid conduit comprising a blind leg connected to an upstream section and a downstream section; a first fluid sampling port provided in the blind leg; and wherein the conduit further comprises a second sampling port.

Additionally another aspect of the invention provides for apparatus for use in sampling multiphase fluid in a fluid transport pipeline, the apparatus comprising: a process fluid conduit comprising a blind leg section connected to an upstream section and a downstream section; a first and a second fluid sampling port, the first fluid sampling port being located in the blind leg section; and at least one fluid sampling conduit which is arranged to be in thermal communication with the process fluid conduit.

The invention may provide a sub-sea and topside sampling apparatus for gas and/or liquid in both multiphase and Wet Gas applications, optionally with a GVF range from 0 to 99.9%.

BRIEF DESCRIPTION OF THE DRAWINGS

For a better understanding of the present invention and to show how the same may be carried into effect, one or more embodiments of the invention are described further below, by way of example, with reference to the accompanying drawings, in which:

FIG. 8 shows another example of the apparatus of the invention in use.

DETAILED DESCRIPTION OF THE DRAWINGS

Figure 1A:
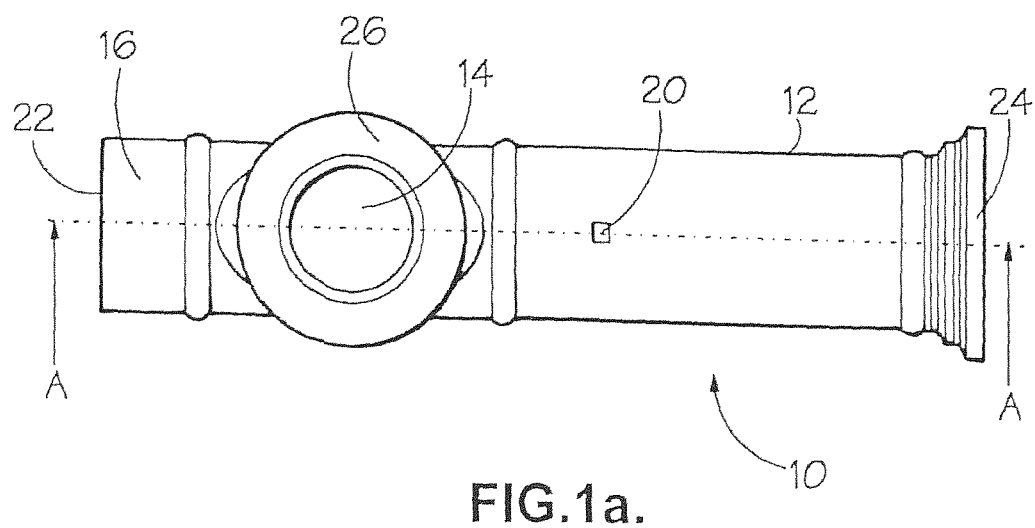
FIG. 1a is a plan view of a conduit for a hydrocarbon transport pipeline according to one or more embodiments of the present invention.
Figure 1B:
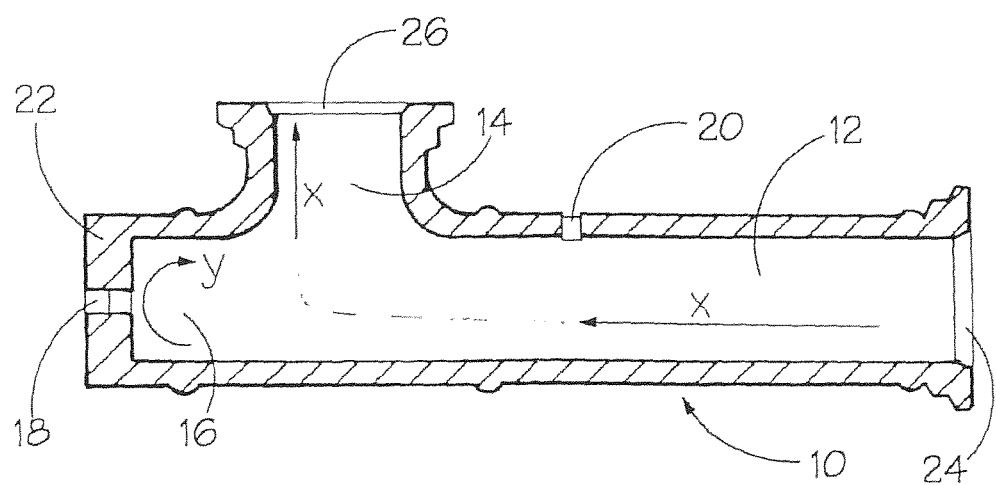
FIG. 1b is a cross-sectional side view, as viewed along line A-A of FIG. 1a, of the conduit for a hydrocarbon transport pipeline according to one or more embodiments of the present invention.

FIGS. 1a and 1b illustrate a process fluid conduit 10 for a hydrocarbon transport pipeline according to one or more embodiments of the present invention. The process fluid conduit 10 comprises an upstream section 12, a downstream section 14 and a blind leg 16. The blind leg 16 extends from the process fluid conduit 10 at the junction where the upstream section 12 of the conduit joins the downstream section 14 of the process fluid conduit 10. The arrangement of the upstream section 12 and downstream section 14 forms a continuous passage for flow of multiphase fluid through the process fluid conduit 10 (see arrows X in the figures which indicate the direction of flow of multiphase fluid through the process fluid conduit 10). Fluid from the flow also circulates in blind leg 16 and this circulatory flow is indicated schematically by arrow Y.

The process fluid conduit 10 further comprises a first sampling port 18 (not shown in FIG. 1a) and a second sampling port 20.

The first sample port 18 is shown located in a central location in an end wall 22 of blind leg 16. However it could be located at any position in the blind leg 16, i.e. on the end wall or side walls of the blind leg 16. The second sample port 20 is shown located in the top of the upstream section 12 of process fluid conduit 10, part-way along the length. It is preferably located in the upper part of the conduit but not necessarily on the top. The second sample port 20 could alternatively be located in the downstream section 14 as shown by reference 20A in FIG. 3 (see later).

Due to the configuration of the process fluid conduit 10, at any particular instant of time, the fluid circulating in the blind-leg 16 is likely to have a greater amount of higher density components of the multiphase fluid than other areas of the process fluid conduit 10, i.e. the blind-leg 16 is likely to have liquid-rich fluid circulating therein. Thus first sample port 18 will generally be used to extract liquid-rich fluid samples. Gas-rich samples can generally be extracted from the second sample port 20 because gaseous components tend to rise by gravity into upper parts of the process fluid conduit 10. A more detailed explanation of this will be provided in relation to FIG. 3 below.

The process fluid conduit 10 comprises a process fluid inlet port 24 at an upstream end of said upstream section 12. The inlet port 24 is configured for coupling with a hydrocarbon transport pipeline. The inlet 24 may optionally comprise a flange section for abutment with a corresponding flange section at the end of the hydrocarbon pipeline to which it is to be coupled. However, it may optionally comprise any suitable type of coupling device, including smaller or larger diameter devices. The arrangement does not require there to be any specific straight length of pipe connected upstream. In addition the process fluid conduit 10 may be permanently or releasably coupled to the pipeline.

The process fluid conduit 10 also comprises a process fluid outlet port 26 at a downstream end of said downstream section 14. The outlet port 26 is also configured for coupling with a hydrocarbon transport pipeline in the same way as the inlet port 24 described above.

Figure 2:
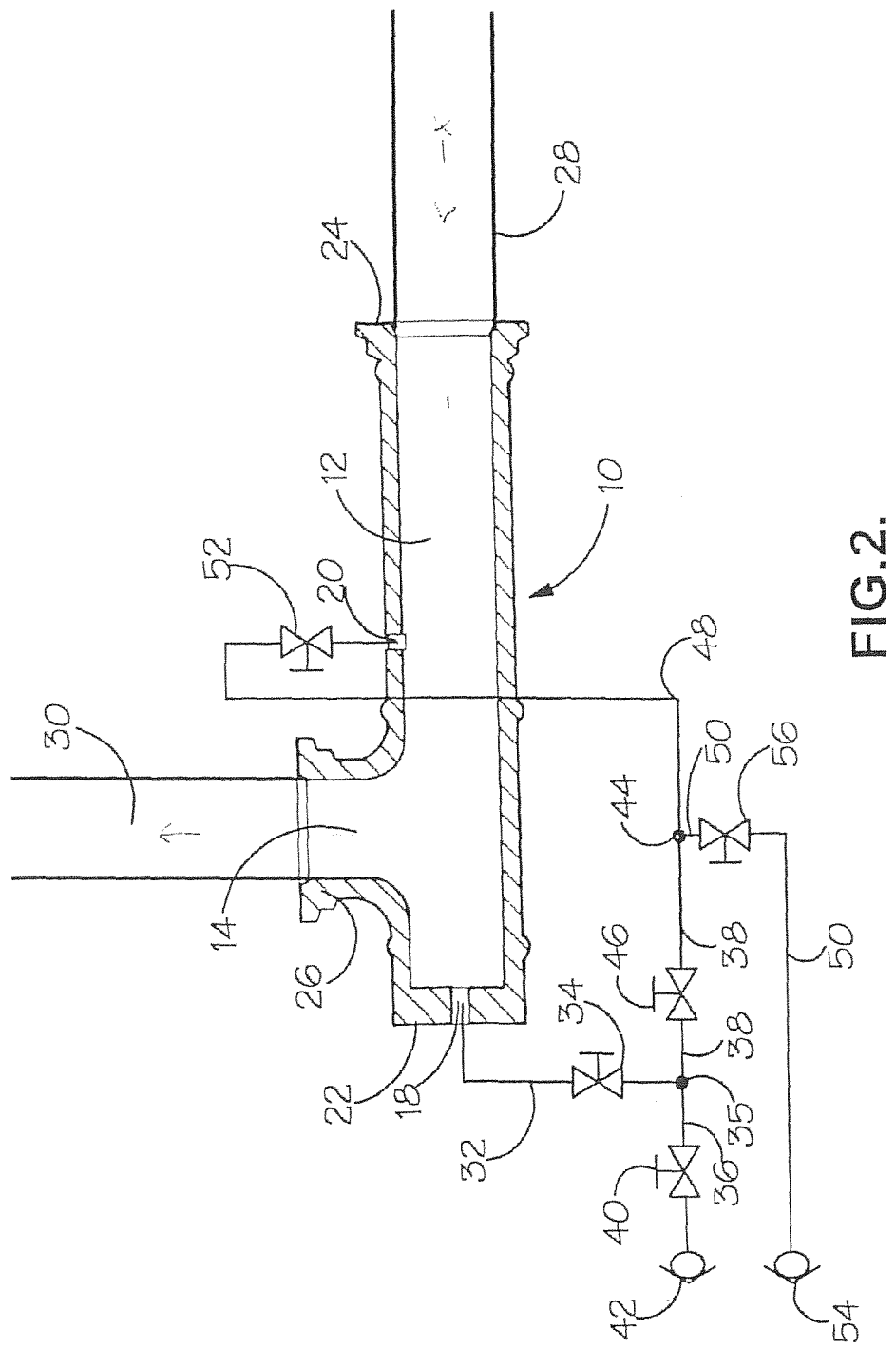
FIG. 2 is a schematic view of a hydrocarbon transport pipeline provided with apparatus according to one or more embodiments of the present invention.

In FIG. 2, the process fluid conduit 10 is shown coupled between an upstream section 28 and a downstream section 30 of a hydrocarbon transport pipeline.

FIG. 2 also schematically illustrates an arrangement of sampling conduits (further described below) and valves which are connected to the sampling ports 18 and 20 and are configured to allow fluid samples to be extracted from the process fluid conduit 10 for measurement. Extracted fluid samples can also be returned to the process fluid conduit 10 using the same arrangement of sampling conduits.

The arrangement of sampling conduits in FIG. 2 will now be described.

Liquid-rich samples are extracted from the first sample port 18 by first sampling conduit 32 controlled by first sample valve 34, and via first junction 35 to a first sample recovery port 42 via output conduit 36 and first output valve 40.

Gas-rich samples are extracted from the second sample port 20 by second sampling conduit 48 controlled by second sample valve 52, and via second junction 44 to a second sample recovery port 54 via output conduit 50 and second output valve 56.

First junction 35 is connected to second junction 44 via a third valve 46.

In an optional arrangement, a sampling tool can engage permanently or detachably with first sample recovery port 42 and second sample recovery port 54. The sampling tool may be operable to extract a sample comprising a liquid-rich component of the multiphase fluid from the process fluid conduit 10 via the first sampling port 18; the first sample conduit 32 (including the first valve 34); the first junction 35; the first output conduit 36 (including the first output valve 40); and the first sample recovery port 42. The third valve 46 must be closed for this.

The sampling tool may also be operable to extract a sample comprising a gas-rich component of the multiphase fluid from the process fluid conduit 10 via: the second sampling port 20; the second sample conduit 48 (including the second sample valve 52); the second junction 44; the second output conduit 50 (including the second output valve 56); and the second sample recovery port 54.

A gas-rich sample may be extracted from the first sample recovery port 42 if a sampling conduit and valve arrangement is used to connect the second sampling conduit 20 to the port 42. For example if the first sample valve 34 is closed, and the third valve 46 and the first output valve 40 are open.

The sampling conduits, or the sampling tool, may also be operable to return extracted samples to the process fluid conduit 10 via the arrangement of sampling conduits. The extracted samples may be returned to the process fluid conduit 10 through first sampling port 18 and/or second sampling port 20, through any suitable combination of conduits, valves, and junctions in the arrangement of sampling conduits illustrated in FIG. 2, as will be clear to a skilled person.

In a further optional arrangement, some or all of the sampling conduits and valves illustrated in FIG. 2 may themselves be located within a sampling tool. In such an arrangement, the sampling tool couples directly to the process fluid conduit 10 via first sampling port 18 and second sampling port 20. The first sample recovery port 42 and second sample recovery port 54 and appropriate barrier fluid valves are then housed within the sampling tool and may be used to convey extracted samples to a measuring apparatus within the sampling tool.

Fluid samples may be withdrawn by the force exerted by a pressure differential which may be created by a flow restriction or by an external pump located for example in the sampling tool. When fluid is extracted from the second sampling port 20 and circulated downstream to the first sampling port 18 there will usually be sufficient pressure differential. However, when extracting fluid from the first port 18 and returning it upstream to the second port 20 there will be insufficient pressure differential and a pump is needed in the circulation path, e.g. in the sampling tool.

The sampling conduits are preferably made as short as possible whilst still enabling combinations of arrangements such as described above to be implemented. By ensuring that the arrangement of sampling conduits is as short as possible, the pressure and temperature of a fluid sample extracted from process fluid conduit 10 and circulating within the arrangement of sampling conduits has little time to change. For example, if measurements are made of the extracted sample close to the point of extraction, then the extracted sample will have little time to cool within the sampling conduits. Thus, the extracted sample is effectively at the same temperature as the process fluid within the hydrocarbon transport pipeline. This enables isobaric and isothermic conditions to be maintained, and ensures that the extracted sample is a representative sample of the fluid within the hydrocarbon transport pipeline. Provided it is a relatively short distance, the temperature will be substantially constant from the blind leg 16 to the first sampling valve 34 since this is directly connected to process flow. However longer sampling conduits cause the sampled fluid to cool, particularly in subsea environments. Insulation of the whole blind leg 16 and the sampling conduits and valves is advantageous to help to maintain isothermal conditions.

The or each valve in the arrangement of sampling conduits may comprise double block valves which provide a process safety barrier.

The sampling tool may comprise an ROV (Remote Operated Vehicle). Such an ROV based sampling tool may be used to obtain samples from the process fluid conduit 10 when the process fluid conduit 10 is in a sub-sea location.

Figure 3:
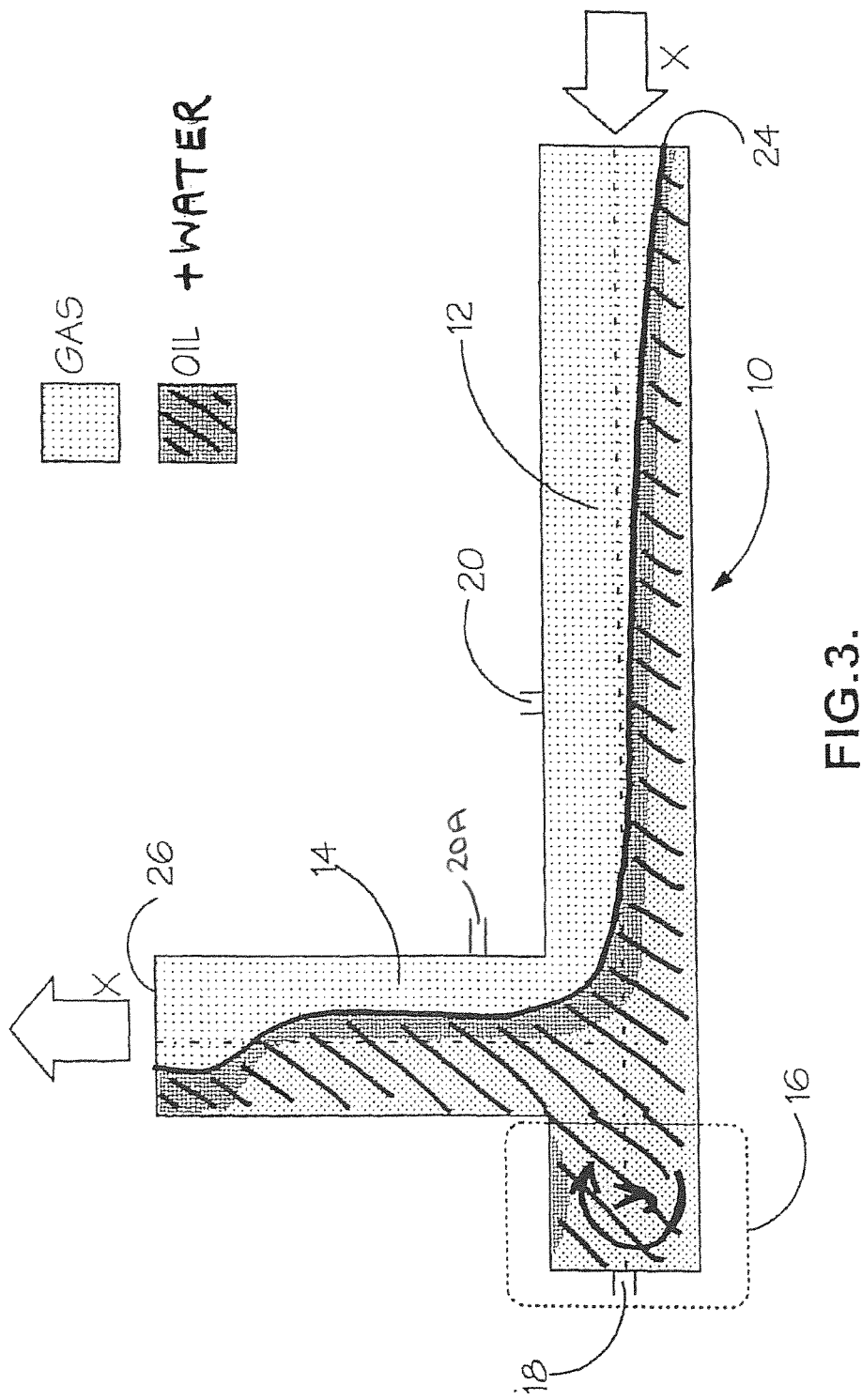
FIG. 3 is a schematic cross-sectional view of apparatus according to one or more embodiments of the present invention when in use.

FIG. 3 illustrates schematically the process fluid conduit 10, showing how gas and liquid is typically distributed within the process fluid conduit 10 in use. The figure aims to illustrate schematically the state of the process fluid conduit 10 at a particular instant of time. As will be appreciated, the ratio of gas/liquid in the process fluid conduit 10 at a different instant of time may be different and/or the distribution of gas and liquid within the conduit may be different to that illustrated, depending on the proportions in the process fluid, speed of flow, pressure, temperature and other conditions.

When multiphase fluid of a well stream enters the process fluid conduit 10, a component phase of the multiphase fluid having the lowest density (e.g. gas as in the illustrated example of FIG. 3) will continuously be drained through the outlet port 26. This draining of the lowest density phase will cause another component phase of the multiphase fluid having a higher density (e.g. water and/or oil as in the illustrated example of FIG. 3) to circulate through the blind-leg 16 of the process fluid conduit 10, as schematically illustrated by the arrow Y.

The lowest density component generally comprises a gas-rich fluid whereas the higher density fluid which circulates through the blind-leg 16 of the process fluid conduit 10 generally comprises a liquid-rich fluid.

As described above in relation to FIG. 2, the liquid-rich fluid which circulates through the blind-leg 16 of the process fluid conduit 10 can be extracted from the process fluid conduit 10 for sampling purposes via the first sampling port 18.

As is apparent from FIGS. 1*a*, 1*b*, 2, 3 and 4, the second sampling port 20 is located on the process fluid conduit 10 upstream of the blind leg 16. The second sampling port 20 is generally in the upper part and preferably at the highest point, of the process fluid conduit 10. Due to its lower density, the gas-rich fluid components will accumulate in the region of the second sampling port 20 so that it can be extracted from the process fluid conduit 10 for sampling purposes via the second sampling port 20.

An alternative position for the second sampling port is shown as 20A in the vertically oriented upstream section 14. In some conditions this position can provide better quality samples. For example when sampled fluid is recycled from the liquid sampling port 18 back to the gas sampling port 20, 20A, having the gas sampling port downstream as at 20A prevents any of the recycled sample entering the blind leg 16 and being part of a subsequent sample from port 18.

This is particularly advantageous when unwanted fluid phases are rejected, particularly if sample storage bottles are used because there may be buffer fluid in the bottles which is at well pressure and may contaminate the intake fluid of recycled upstream.

Usually this would only present a minor problem but can be more significant at high GVF when sampling water because sampling is done in several steps. Also at high GVF and low water cut recycling upstream may slow down the water enrichment process.

Figure 4:
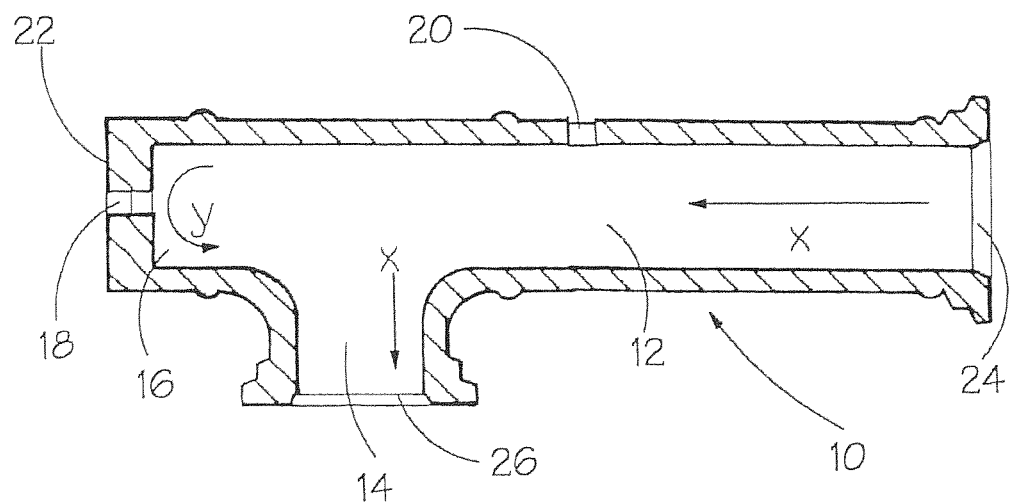
FIG. 4 is a cross-sectional side view of apparatus for a hydrocarbon transport pipeline according to one or more embodiments of the present invention.

The downstream position 20A for the gas sampling port can also be used for the "upside down" configuration shown in FIG. 4 because a pocket of gas forms on this side just after the turn in both embodiments.

As will be appreciated from the above description, the process fluid conduit 10 has the effect of at least partially separating liquid and gas phases of the multiphase fluid and making the two phases available through the conduit for sampling at line conditions. Thus, representative samples enriched in the volumetric proportion of gas are likely to be obtained from second port 20 and samples enriched in the volumetric proportion of liquid from first port 18. The liquid phase comprises a mixture of water and oil which will be mixed to an extent dependent on many factors including temperature, pressure and the speed of flow.

In an optional arrangement, the sampling conduits can be heated to maintain the temperature of extracted samples through the sampling conduits. Such an arrangement may provide for active management of hydrate issues may inhibit waxing problems. These waxing problems include wax settling inside a conduit. The arrangement of sampling conduits can be particularly vulnerable to such problems. Therefore, it is of importance to ensure that the flow within the arrangement of sampling conduits is at the same pressure and temperature as the process fluid conduit 10 to inhibit problems of unwanted deposition of wax, asphaltene, hydrates, scale or other materials.

Figure 6:
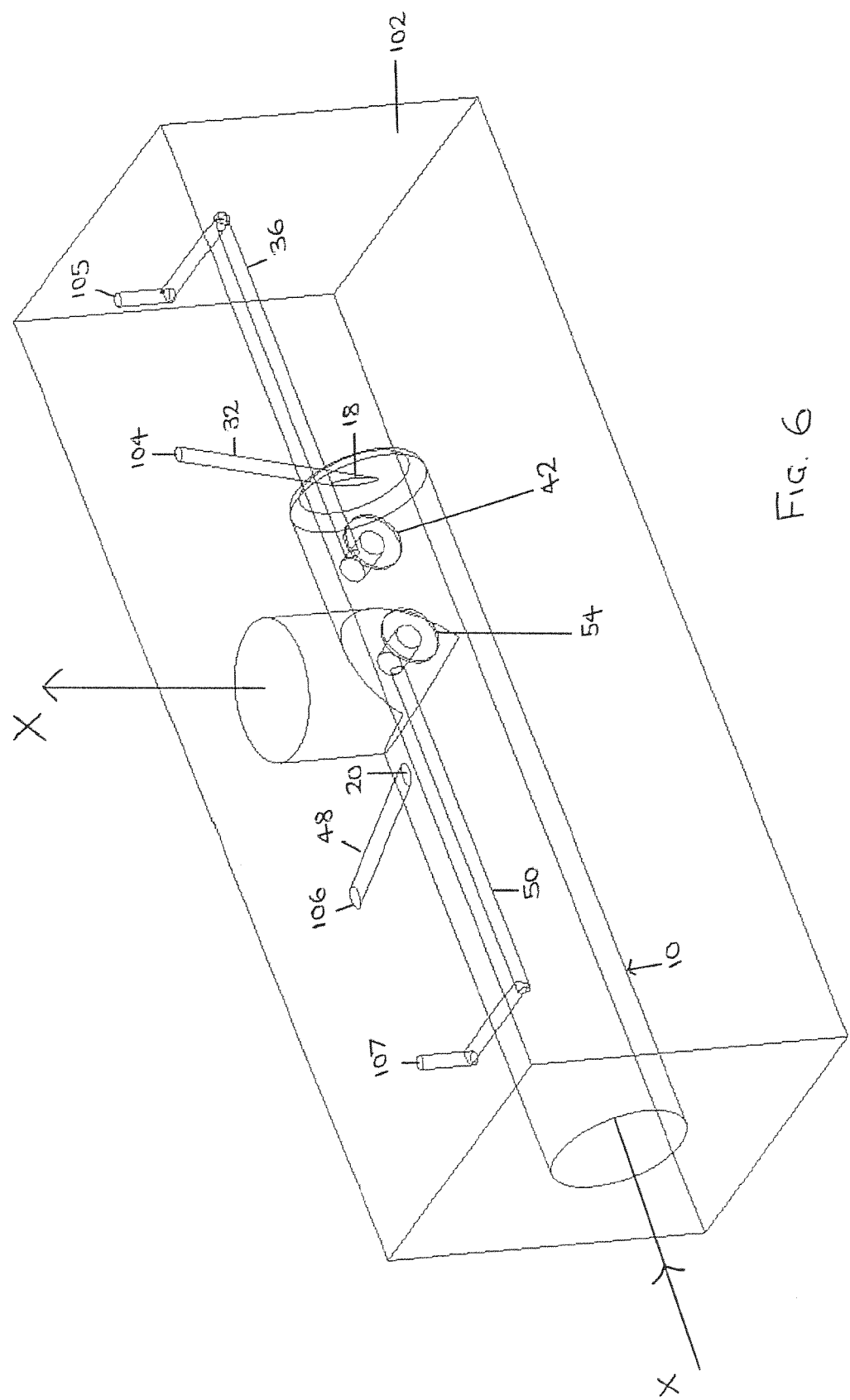
FIG. 6 is a see-through diagram illustrating further detail of the apparatus of the invention.

This can be achieved by forming at least some of the sampling conduits and the process fluid conduit 10 in an integrated unit. One example of such a unitary block is shown in FIG. 6 which is described below. A block of thermally conductive material such as metal may be used, in which the conduits are embedded or formed, e.g. by boring. Such a block of metal serves to maintain the sample fluid temperature the same as or close to the temperature of the process fluid in the process line. The diameter of these sampling conduits can be optimized to minimise any pressure loss and thus maintain isobaric conditions. The diameter of the sampling conduits is optimized for low friction but to ensure a capillary effect to avoid or reduce separation of liquid and gas inside the conduits. Typically the preferred diameter of the sampling conduits will be between a few (3-4) millimeters and 2-3 centimeters.

FIG. 6 shows a three dimensional representation of apparatus of the invention in which the process fluid conduit 10 and the sampling conduits are all formed integrally in a block 102 of thermally conductive material such as metal. Steel is particularly advantageous. The liquid phase sample recovery port 42 and the gas phase sample recovery port 54 are shown in the side of the block 102. The liquid sampling port 18 is connected by integral sampling conduit 32 to a port 104 at the top of the block 102. The liquid sample recovery port 42 is connected by integral conduit 36 to port 105 at the top of the block. Ports 104 and 105 are connected by conduits and valves, as illustrated in FIG. 2 and/or FIG. 5 which may be in a separate unit either permanently connected or located in a sampling tool which may be releasably attached.

Similarly the gas sampling port 20 is connected by conduit 48 to port 106, and gas recovery port 54 by conduit 50 to port 107. Port 106 and 107 are similarly connected by a sampling tool It can clearly be seen that the gas and liquid sampling conduits 48, 50, 32, 36 are integral to the block 102 and are thus heated by the heat of the process fluid in the process fluid conduit 10 thus maintaining substantially isothermal and isobaric conditions for the sampling fluids.

In FIG. 6 the sample recovery ports 42 and 54 are shown on the side of the block but they may alternatively be arranged on the top or bottom of the block depending upon the orientation required for access from a sampling tool and/or ROV.

The temperature of the extracted sample can alternatively or additionally be maintained by using a heat conductive material, wrapped around the sampling conduits, and arranged to convey process fluid heat to the sampling conduits.

In a further optional arrangement, the sampling conduits may be insulated with a defined layer of insulating material. Heat conducting material and insulation can be combined for optimum effect.

In a further optional arrangement, fluid can be extracted from the process fluid conduit 10 and circulated through the arrangement of sampling conduits from first sampling point 18 to second sampling point 20 and vice-versa to pre-heat the lines prior to sample extraction. Again, this helps to inhibit heat loss from the extracted sample when in the arrangement of sampling conduits.

The process fluid conduit 10 may be installed in any orientation, for example to permit vertical downwards flow. Such an arrangement is illustrated in FIG. 4. In this case, process fluid conduit 10 is arranged with the outlet port 26 extending in a downwards direction and is configured such that the second sampling port 20 is on an opposite side of the process fluid conduit 10 to that illustrated in FIGS. 1*a*, 1*b* and 2 since this is now the upper part of the process fluid conduit 10.

In the illustrated arrangements of FIGS. 1*b*, 2 and 3 the downstream section 14 is shown upstanding from the process fluid conduit 10. However, in the arrangement illustrated in FIG. 4, the downstream section 14 descends from the process fluid conduit 10. The downstream section 14 need not be vertical and may extend from the process fluid conduit 10 at any angle subject to the conduit forming a three-legged junction including a blind leg. The junction may thus be generally T or Y shaped. Of course, in such an arrangement, the second sampling port 20 needs to be suitably located on the upper part of process fluid conduit 10 to enable gas-rich fluid to be extracted.

Locating the arrangement of sampling conduits as far as possible close to the process fluid conduit 10 and within insulation ensures that the arrangement of sampling conduits is at or close to the process temperature. At least some of the sampling conduits may be located within the wall of the process fluid conduit 10 so that they are heated by the process fluid heat from the process fluid conduit 10. Either of these arrangements will usually be useful for inhibiting formation of hydrates and will reduce deposition problems, e.g. of any type of organic or inorganic solid deposit, wax, asphaltene, hydrate, scale, sand, clay or other materials. It is also advantageous to arrange the orientation of the sampling conduits to avoid deposits settling in the parts, i.e. to arrange them to extend at an angle to the horizontal.

Optionally, the sampling conduits can in addition be equipped with chemical injection points to further reduce flow assurance risks, i.e. waxing problems and hydrate formation due to decreases in temperature.

If the sampling apparatus of the present invention is used in a subsea sampling operation, samples obtained in the manner described above can be circulated or drained through or into sampling bottles which can be temporarily installed on the process fluid conduit 10. The samples can be retrieved from the sampling bottles by means of an ROV intervention vessel, or samples could be analysed at or near a permanently installed conduit.

An ROV may carry a sampling tool. Sampled fluid may be extracted and circulated through the sampling tool by use of a pump. As described above, a liquid-rich sample may be extracted from the process fluid conduit 10 (via first sampling port 18), a measurement may be performed on the extracted liquid-rich sample in the ROV, and the extracted liquid-rich sample may be returned to the process fluid conduit 10 (via second sampling port 20). Such a system may have sampling bottles installed on the ROV carried tool, or it may have analytical capabilities precluding the need for sample recovery. "Smart" sampling tools are known which can analyze samples in situ and detect whether the sample is suitable for a particular purpose, automatically recirculating and wrong or inadequate samples.

Types of ROV which might be suitable for use as described above are disclosed in international patent applications WO 2010/106499 and WO 2010/106500.

As noted previously, the present invention may be suitable for both topside and sub-sea applications. Sub-sea sampling of a multiphase fluid differs from topside sampling due to ambient conditions, typically cold water and large depths combined with high process pressure and lack of access. Additionally, hydrates, wax and scale may form during the fluid sampling process (as noted above). Particularly in deep sea situations the hydrostatic external pressure from the surrounding sea water is very high and is higher than the internal pressure such as process line pressure. In this case to collect a sample requires control of the pressure differential between the line pressure and the collected fluid pressure. This is usually achieved using a pumping system.

When located in a sub-sea environment, the sampling apparatus may be integrated into the subsea infrastructure using any one of at least three different configurations, namely:

i Inline, as mounted into a rigid well jumper for the purpose of connecting a Christmas tree to a manifold;

ii Manifold installed as a central unit where different wells are commingled; or iii Installed on to a Christmas tree as a fixed unit or as a part of a retrievable structure.

Optionally, the inlet port 24 and upstream section 28 of hydrocarbon transport pipeline are coupled by way of flanges and/or a weld, or any other suitable type of coupling device.

The process fluid conduit 10 may optionally be connected to a multiphase flow-meter (MPFM). In such an arrangement, the outlet port 26 of the process fluid conduit 10 may be connected to an inlet port of the multiphase flow-meter by a weld or a flange and bolt arrangement. The blind leg of the process fluid conduit 10 serves to condition the process fluid to make it more suitable for the multiphase flow meter because it has the effect of mixing the fluid and generating a less sluggy flow.

The blind leg 16 may be any length but the optimum length is such as to achieve adequate mixing or conditioning of the fluid without it cooling substantially. The length may be between 10 and 200% of the nominal diameter of the process fluid conduit 10. If the blind leg 16 is too short then insufficient mixing occurs and a suitable liquid rich sample is not achieved. If the blind leg 16 is too long then circulation slows or stops so the fluid cools.

When the sampling conduits and process fluid conduit 10 are all made as an integral block, the resulting unit may be formed in a retrievable package and be removably connected into a pipeline. In this way it can be retrieved for servicing or repair. This is particularly advantageous since solids such as hydrates and salts can collect in the sampling conduits and block them, and servicing and repair is very difficult in situ if the pipeline is located in deep sea locations.

Figure 5:
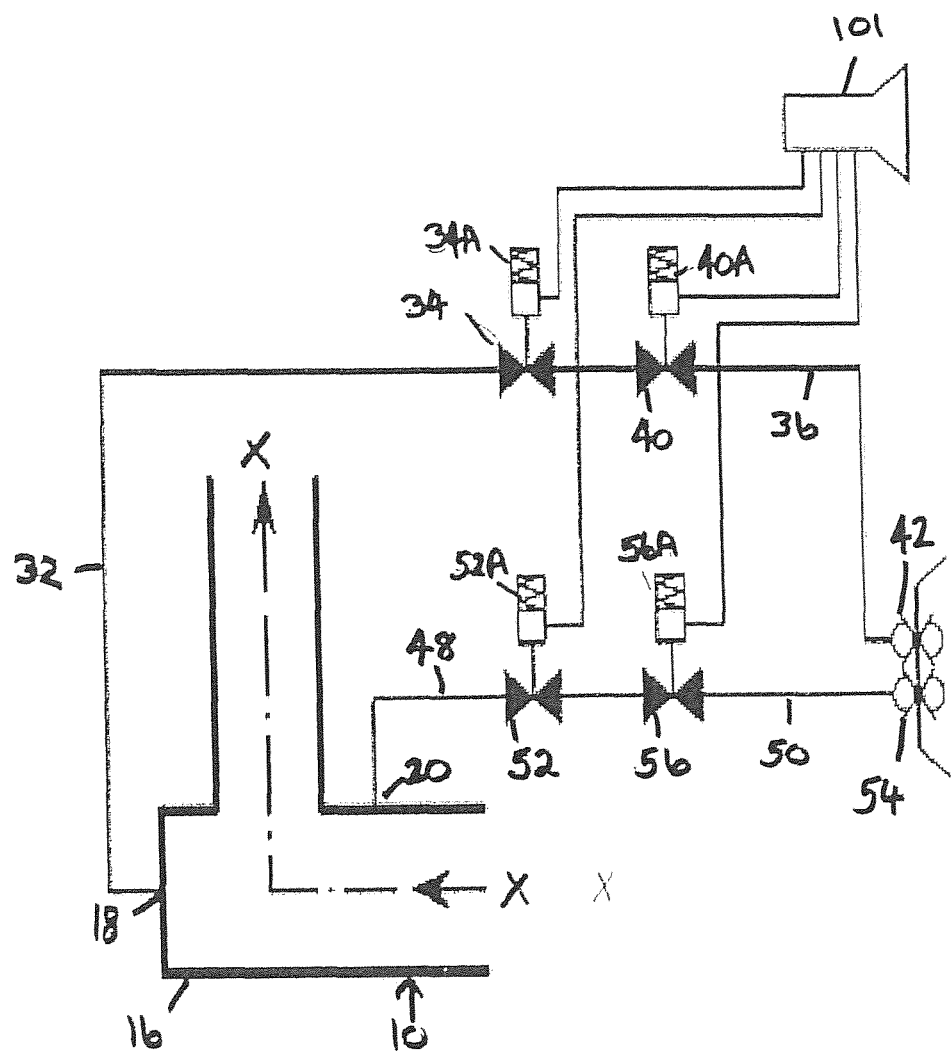
FIG. 5 is a schematic diagram illustrating apparatus of the invention.

FIG. 5 is another schematic diagram showing an arrangement of sampling conduits. This is similar to the arrangement in FIG. 2 and like reference numerals have been used. Each of the valves 34, 40, 52 and 56 has a valve actuator 34A, 40A, 52A and 56A respectively which are all connected to a valve actuation control unit 101. In this arrangement any circulation of the sampled fluid would take place via the sample recovery ports 42 and 54.

Figure 7:
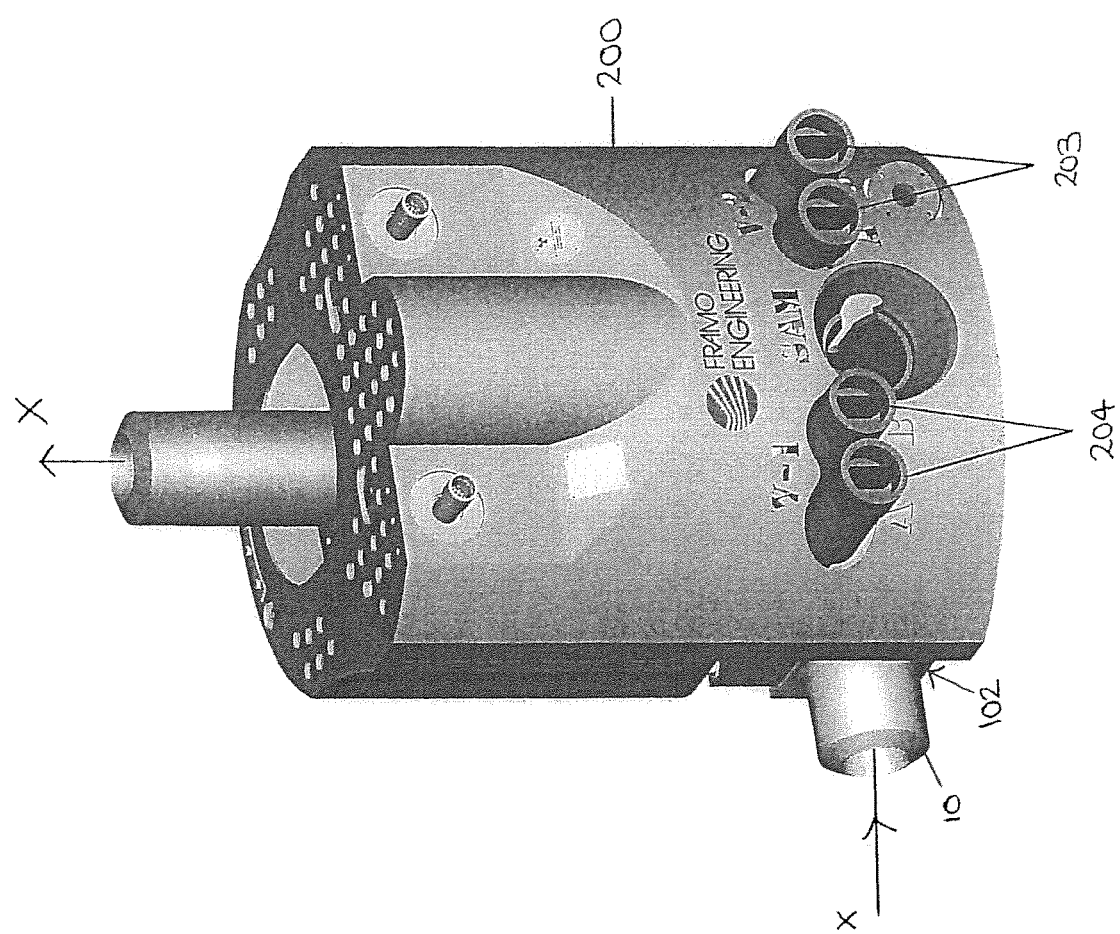
FIG. 7 shows one example of the apparatus of the invention in use.

FIG. 7 illustrates one example of the sampling apparatus integrated with a multiphase flow meter 200. Sample recovery ports for liquid are indicated at 204 and for gas at 203, and the process flow direction is indicated by arrows X.

FIG. 8 illustrates another example of a sampling apparatus integrated with a multiphase flow meter. In this example the block 102 comprising the sampling apparatus, including the process fluid conduit 10 with the blind leg, is located on top of the multiphase flow meter 200 and process fluid flows downward through the meter instead of upward as in FIG. 7. The process fluid flows into and on top of the apparatus via the two hub connectors 205, 206 at the bottom of the unit. This arrangement is advantageous because it can easily be removed from the process flow for servicing, cleaning or repair. The hub connections can be disengaged and the whole unit lifted by engagement of a tool or ROV with coupling 207 shown at the top.

In FIGS. 7 and 8 the sample recovery ports for liquid and gas are shown extending laterally. However they could be arranged to extend vertically, and to provide easier access for a detachable sampling tool carried by or integral with an ROV.

The invention claimed is:

1. Apparatus for use in sampling multiphase fluid in a fluid transport pipeline, the apparatus comprising:

a process fluid conduit comprising a blind leg connected to an upstream leg and a downstream leg, wherein the upstream leg is substantially axially aligned with the blind leg, and the upstream leg is axially angled relative to the downstream leg to form a three-legged junction;
a fluid inlet port in the upstream leg, wherein the fluid inlet port is substantially axially aligned with the upstream leg and the blind leg;
a first fluid sampling port provided in the blind leg to receive a first fluid sample; and
a second fluid sampling port provided in one of the upstream leg and the downstream leg downstream of the fluid inlet port, and spaced apart from the first fluid sampling port to receive a second fluid sample; and
wherein the process fluid conduit, the first fluid sampling port, and the second fluid sampling port are integrally formed in a block of material.

2. Apparatus according to claim 1 comprising means for circulating fluid from the first fluid sampling port to the second fluid sampling port.

3. Apparatus according to claim 2 wherein the means for circulating fluid is arranged to circulate fluid from a sampling port which is at a higher pressure to a sampling port at a lower pressure.

4. Apparatus according to claim 1 comprising at least one sampling conduit connected to the first fluid sampling port.

5. Apparatus according to claim 4 wherein the at least one sampling conduit is integrally formed in the block of material; and
wherein the block of material comprises a thermally conductive material.

6. Apparatus according to claim 1, wherein, when the process fluid conduit is in a first configuration, the downstream leg extends substantially vertically upwards from the three-legged junction and the second fluid sampling port is located in an uppermost part of a wall of the process fluid conduit in the upstream leg.

7. Apparatus according to claim 1, wherein, when the process fluid conduit is in a second configuration, the downstream leg extends substantially vertically downwards from the three-legged junction and the second fluid sampling port is located in an uppermost part of a wall of the process fluid conduit in the upstream leg.

8. Apparatus according to claim 1 further comprising at least one sampling conduit connected to the process fluid conduit and means for heating the at least one sampling conduit.

9. Apparatus according to claim 4 wherein the at least one sampling conduit is arranged in a non-horizontal orientation.

10. Apparatus according to claim 1 further comprising a multiphase flow meter.

11. Apparatus according to claim 1 further comprising a sampling tool which is attachable to and detachable from at least one of the first and second fluid sampling ports;
wherein the sampling tool comprises circulating means that is operated remotely.

12. A system for sampling fluid from a multi-phase hydrocarbon stream comprising apparatus according to claim 1 and a remotely operated system comprising means to connect the first fluid sampling port located in the blind leg to the second fluid sampling port and to circulate fluid from the first fluid sampling port to the second fluid sampling port at substantially isothermal and isobaric conditions.

13. A system according to claim 12 wherein the remotely operated system comprises means to perform at least one measurement on the circulating fluid at substantially isothermic and isobaric conditions.

14. A system according to claim 12 or 13 comprising means to capture a sample of fluid in at least one sealable container.

15. Apparatus for use in sampling multiphase fluid in a fluid transport pipeline, the apparatus comprising:
a process fluid conduit comprising:
a blind leg;
an upstream leg with a fluid inlet port; and
a downstream leg with a fluid outlet port and axially angled relative to the upstream leg;
wherein the blind leg extends from the angled junction of the upstream leg and the downstream leg;
a first fluid sampling port provided in the blind leg to receive a first fluid sample; and
a second fluid sampling port provided in one of the upstream leg and the downstream leg between the fluid inlet port and the fluid outlet port, and spaced apart from the first fluid sampling port to receive a second fluid sample, wherein the second fluid sampling port extends from the interior of the one of the upstream leg and the downstream leg, through the one of the upstream leg and the downstream leg, and to the exterior of the one of the upstream leg and the downstream leg to deliver the second fluid sample to the exterior of the one of the upstream leg and the downstream leg.

16. Apparatus according to claim 15 comprising means for circulating fluid from the first fluid sampling port to the second fluid sampling port.

17. Apparatus for use in sampling multiphase fluid in a fluid transport pipeline, the apparatus comprising:
a process fluid conduit comprising a blind leg section connected to an upstream section and a downstream section;
a first and a second fluid sampling ports, the first fluid sampling port being located in the blind leg section;
at least one fluid sampling conduit which is arranged to be in thermal communication with the process fluid conduit;
wherein the at least one fluid sampling conduit comprises:
a first sampling conduit connected to the first sampling port, the first sampling conduit coupled to a first sample recovery port via first junction; and
a second sampling conduit connected to the second sampling port, the second sampling conduit coupled to a second sample recovery port via a second junction;
wherein the first junction is connected to the second junction via a valve.

18. Apparatus according to claim 17 wherein the process fluid conduit, the first sampling conduit, and the second sampling conduit are integrally formed in a solid block of thermally conductive material and at least one process fluid or sampling conduit is bored into the material.

19. Apparatus according to claim 15, comprising at least one sampling conduit connected to the first fluid sampling port.

20. Apparatus according to claim 15, further comprising:
a first sampling conduit connected to the first fluid sampling port, the first sampling conduit coupled to a first sample recovery port via a first conduit junction; and
a second sampling conduit connected to the second fluid sampling port, the second sampling conduit coupled to a second sample recovery port via a second conduit junction;

wherein the first conduit junction is connected to the second conduit junction via a valve.

21. Apparatus according to claim 15, wherein, when the process fluid conduit is in a first configuration, the downstream leg extends substantially vertically upwards from the junction of the upstream leg and the downstream leg and the second sampling port is located in an uppermost part of a wall of the process fluid conduit in the upstream leg.

22. Apparatus according to claim 15, wherein, when the process fluid conduit is in a second configuration, the downstream leg extends substantially vertically downwards from the junction of the upstream leg and the downstream leg and the second sampling port is located in an uppermost part of a wall of the process fluid conduit in the upstream leg.

23. Apparatus according to claim 15, further comprising a heat conductive material at least partially surrounding at least one sampling conduit;
   wherein the at least one sampling conduit is connected to at least one of the first fluid sampling port and the second fluid sampling port.

24. Apparatus according to claim 15, wherein the downstream leg extends from the junction of the upstream leg and the downstream leg in a direction that is perpendicular to both the upstream leg and the blind leg; and
   wherein the blind leg extends from the junction of the upstream leg and the downstream leg in a direction that is aligned with the upstream leg and perpendicular to the downstream leg.

25. Apparatus according to claim 24, wherein the blind leg has a length that is between 10% and 200% of a diameter of the process fluid conduit.

26. Apparatus according to claim 17, wherein the upstream section, the downstream section, and the blind leg form a three-legged junction.

27. Apparatus according to claim 26, wherein the downstream section extends from the three-legged junction in a direction that is perpendicular to both the upstream section and the blind leg; and
   wherein the blind leg extends from the three-legged junction in a direction that is aligned with the upstream section and perpendicular to the downstream section.

28. Apparatus according to claim 27, wherein the blind leg has a length that is between 10% and 200% of a diameter of the process fluid conduit.

* * * * *